US008173827B2

(12) United States Patent
Chang et al.

(10) Patent No.: US 8,173,827 B2
(45) Date of Patent: May 8, 2012

(54) METHOD FOR PREPARING POROUS ORGANIC-INORGANIC HYBRID MATERIALS, POROUS ORGANIC-INORGANIC HYBRID MATERIALS OBTAINED BY THE METHOD AND CATALYTIC USES OF THE MATERIALS

(75) Inventors: Jong-San Chang, Daejeon (KR); Young Kyu Hwang, Daejeon (KR); Sung Hwa Jhung, Daejeon (KR); Do-Young Hong, Yongin (KR); You-Kyung Seo, Busan (KR); Gerard Ferey, Versailles (FR); Christian Serre, Versailles (FR)

(73) Assignee: Korea Research Institute of Chemical Technology, Daejeon (KR)

( * ) Notice: Subject to any disclaimer, the term of this patent is extended or adjusted under 35 U.S.C. 154(b) by 224 days.

(21) Appl. No.: 12/473,048

(22) Filed: May 27, 2009

(65) Prior Publication Data

US 2009/0227446 A1    Sep. 10, 2009

Related U.S. Application Data

(63) Continuation-in-part of application No. PCT/KR2007/006004, filed on Nov. 26, 2007.

(30) Foreign Application Priority Data

Nov. 27, 2006  (KR) .................. 10-2006-0117549
Jun. 27, 2007  (KR) .................. 10-2007-0063881

(51) Int. Cl.
*C07F 9/00*    (2006.01)
(52) U.S. Cl. ............ 556/44; 556/61; 556/147; 502/167; 502/168; 502/150; 502/170
(58) Field of Classification Search ............. 556/44, 556/61, 147; 502/167, 168, 150, 170
See application file for complete search history.

(56) References Cited

U.S. PATENT DOCUMENTS 4,778,666 A    10/1988    Chu et al.
(Continued)

FOREIGN PATENT DOCUMENTS

JP    2004-262945    9/2004
(Continued)

OTHER PUBLICATIONS

Ferey, G. et al., "A Chromium Terephthalate-Based Solid with Unusually Large Pore Volumes and Surface Area," *Science*, 309, 2040 (2005).

(Continued)

*Primary Examiner* — Melvin Mayes
*Assistant Examiner* — Melissa Stalder
(74) *Attorney, Agent, or Firm* — Nelson Mullins Riley & Scarborough LLP; EuiHoon Lee, Esq.

(57) ABSTRACT

The present invention relates to a method for preparing iron-containing porous organic-inorganic hybrid materials where the organic compound ligand is bonded to a central metal and has a large surface area and pores of molecular size or nano size, by irradiating microwaves instead of heat treatments such as the conventional electric heating, etc. as the heat source of the hydrothermal or solvothermal synthesis reaction, after reacting a metal or metal salt and organic compound to form crystal nuclei by a predetermined pre-treatment operation in the presence of a solvent.

In another aspect, a method of the present invention further comprises the step of purifying the obtained porous organic-inorganic hybrid materials by treating them with inorganic salt. In particular, a method of the present invention is characterized by not using a hydrofluoric acid.

11 Claims, 8 Drawing Sheets

U.S. PATENT DOCUMENTS 6,893,564 B2      5/2005    Mueller et al.
2002/0147293 A1*   10/2002   O'Gara ........................... 528/10

FOREIGN PATENT DOCUMENTS

| JP | 2005-528204 | 9/2005 |
|---|---|---|
| WO | 2008/072896 A1 | 6/2008 |

OTHER PUBLICATIONS

Ferey, Gerard et al., "A Hybrid with Giant Pores Prepared by a Combination of Targeted Chemistry, Simulation, and Powder Diffraction," *Angew. Chem. Int. Ed.*, 43:6296-6301, 2004.

Frey, Grard et al., "Crystallized Frameworks with Giant Pores: Are There Limits to the Possible?," Accounts of Chemical Research, 38 (4): 217-225. 2005.

Guillou, Nathalie et al., "The Chirality, Porosity, and Ferromagnetism of a 3D Nickel Glutarate with Intersecting 20-Membered Ring Channels," Angew. Chem. Int. Ed., 42:5314-5317, 2003.

James, Stuart L. et al., "Metal-organic frameworks," Chem. Soc. Rev., 32:276-288, 2003.

Jhung, Sung Hwa et al., "Microwave Synthesis of a Nanoporous hybrid Material, Chromium Trimesate," Bulletin of Korean Chemical Society, vol. 26(6):880, 2005.

Kitagawa, Susumu et al., "Functional Porous Coordination Polymers," Angew. Chem. Intl. Ed., 43:2334-2375, 2004.

Park, Sang-Eon et al., "Supramolecular interactions and morphology control in microwave synthesis of nanoporous materials," Catalysis Surveys from Asia, vol. 8(2):91, 2004.

Rosseinsky, M.J., "Recent developments in metal—organic framework chemistry: design, discovery, permanent porosity and flexibility," Microporous and Mesoporous Materials, vol. 73:15-30, 2004.

Choi, Jae Yong et al., "Microwave Synthesis of a Porous Metal-Organic Framework, Zinc Terephthalate MOF-5," Bull. Korean Chem. Soc., vol. 27(10):1523-1524 (2006).

Horcajada, Patricia et al., "Synthesis and catalytic properties of MIL-100(Fe), an iron (III) carboxylate with large pores," Chem. Comm., pp. 2820-2822 (2007).

Jhung, Sung Hwa et al., "Microwave Synthesis of Chromium Terephthalate MIL-101 and its Benzene Sorption Ability," Adv. Mater., vol. 19:121-124 (2007).

European Office Action for Application No. 07834299.5. dated Aug. 17, 2011.

* cited by examiner

METHOD FOR PREPARING POROUS ORGANIC-INORGANIC HYBRID MATERIALS, POROUS ORGANIC-INORGANIC HYBRID MATERIALS OBTAINED BY THE METHOD AND CATALYTIC USES OF THE MATERIALS

This application is a Continuation in part of PCT Application No. PCT/KR2007/006004, filed on Nov. 26, 2007, which claims priority to, and the benefit of, Korean Patent Application No. 10-2006-0117549, filed on Nov. 27, 2006, and Korean Patent Application No. 10-2007-0063881, filed on Jun. 27, 2007. The contents of the aforementioned applications are hereby incorporated by reference.

BACKGROUND

The present invention relates to a method for preparing porous organic-inorganic hybrid materials and their catalytic use. More particularly, the present invention relates to porous organic-inorganic hybrid materials containing metal and a method for preparing the materials. That is, it relates to a novel method for preparing porous organic-inorganic hybrid materials containing metal such as iron, which can be used not only for adsorbents, gas storing materials, sensors, catalysts and catalyst carriers, etc., but also for including guest molecules smaller than the pore size or separating molecules larger than pore size, since these porous organic-inorganic hybrid materials have a large surface area and a pore of a molecular size or nano size, wherein the organic compound ligand is bonded to a central metal by the preparing porous organic-inorganic hybrid materials containing metal such as iron by irradiating microwaves instead of heat treatments such as the conventional electric heating, etc. as a heat source of the hydrothermal or solvothermal synthesis reaction after forming crystal nuclei by pre-treating a metal or metal salt and an organic compound in the presence of a solvent. Also, the method for preparing porous organic-inorganic hybrid materials of the present invention further comprises a step of purifying the obtained porous organic-inorganic hybrid materials by treating them with an inorganic salt. Further, the present invention relates to a novel method for preparing porous organic-inorganic hybrid materials wherein use of hydrofluoric acid has been eliminated and the porous organic-inorganic hybrid materials obtained by said preparation method can be used as a heterogeneous catalyst.

The porous organic-inorganic hybrid materials prepared according to the present invention can be defined as porous organic-inorganic polymer compounds formed by binding a central metal ion with an organic ligand, wherein the central metal ion may be an iron ion. The compounds are a crystalline compounds having a pore structure of a molecular size or nano-size and containing both an organic and an inorganic compounds within the framework structure.

The term "porous organic-inorganic hybrid materials" has a broad meaning, and in general, it is also referred to as "porous coordination polymers" [Angew. Chem. Intl. Ed., 43, 2334 (2004)], or "metal-organic frameworks" [Chem. Soc. Rev., 32, 276 (2003)].

At present scientific research is focused on materials developed by integrating molecular coordination bonding with material science. Said materials have large surface area and pores of a molecular size or nano size, and thus can be used not only for adsorbents, gas storing materials, sensors, membranes, functional thin films, catalysts and catalyst carriers, etc., but also for including guest molecules smaller than their pore size or separating molecules depending on sizes of the molecules by using their pores. Thus, they have gained much importance.

Porous organic-inorganic hybrid materials have been prepared by various methods. Usually, they have been prepared by a hydrothermal synthesis reacting at high temperature by using water as a solvent or by reacting near room temperature using solvent diffusion, or a solvothermal synthesis using an organic solvent [Microporous Mesoporous Mater., 73, 15 (2004); Accounts of Chemical Research, 38, 217 (2005)].

Such porous organic-inorganic hybrid materials have been prepared through crystallization at a synthesis temperature of at least the boiling point of a solvent or solution mixture under an autogeneous pressure using water or a suitable organic solvent, as in methods for preparing other inorganic porous materials such as zeolites or mesoporous compounds.

The hydrothermal preparation methods mentioned above have problems such that an excessive amount of energy is consumed because usually a reaction time of at least several days is required for obtaining complete crystalline organic-inorganic hybrid materials since the nuclei formation or crystallization process is very slow. In particular, it shows a very low efficiency since the reaction is proceeded only by a batch-type manner [Angew. Chem. Intl. Ed. vol. 42, p. 5314 (2003); Angew. Chem. Intl. Ed. vol. 43, p. 6296 (2004)].

In order to overcome these problems, a method to maximize the efficiency by applying microwaves to the synthesis of porous inorganic materials including zeolites has been suggested, and methods applying microwaves were known in some patents and articles published since 1988 [U.S. Pat. No. 4,778,666; Catal. Survey Asia, vol. 8, p. 91 (2004)]. In many cases, it has been reported that the synthesis time has been decreased and porous inorganic materials can be continuously synthesized when microwaves were used compared to the hydrothermal synthesis by conventional heating.

Unlike the porous inorganic materials above, porous organic-inorganic hybrid materials have been recognized to have unique features that they can be used not only for catalysts, catalyst carriers, adsorbents, ion exchanging materials and gas storing materials, but also for storing, preparing and separating nanomaterials, and for nanoreactors, due to their characteristics such as large surface area, crystalline structure of a very high regularity and relatively high thermal stability, etc. In this regard, Cr-MIL-100, which is an organic-inorganic hybrid material of MIL-100 structure (MIL: Materials of Institute Lavoisier), has been reported [Bulletin of Korean Chemical Society vol. 26, p. 880 (2005)].

However, as for the organic-inorganic hybrid materials containing Cr as stated above, due to the Cr component that is harmful to the human body, its use is relatively limited. In particular, iron-organic-inorganic hybrid materials having Fe as a central metal which is not harmful to the human body cannot be easily formed by the synthetic method of the organic-inorganic hybrid materials containing the Cr component, and thus development of a novel preparation method for said materials has been needed.

Also, as for the synthesis of porous organic-inorganic hybrid materials by hydrothermal synthesis, in general, a mixed-acid comprising nitric acid, hydrofluoric acid, etc. is used in order to regulate the rate of forming crystals. As for representative porous organic-inorganic hybrid materials prepared by the hydrothermal synthesis, MIL-100 (Cr) represented by formula of $Cr_3O(H_2O)_2F[C_6H_3-(CO_2)_3]_2 \cdot nH_2O$ (n~14.5) and MIL-101 (Cr) represented by formula of $Cr_3F(H_2O)_2O[C_6H_4(CO_2)_2]_3 \cdot nH_2O$ (n~25) have been reported [Science 23, 2040 (2005); Accounts of Chemical Research, 38, 217 (2005)]. The organic-inorganic hybrid materials of a metal-organic framework structure where the Cr component is substituted by another metal have not been reported yet. In the meantime, the organic ligand present in the porous organic-inorganic hybrid materials prepared by above conventional processes, brought about small surface area and pore volume.

Therefore, development of porous organic-inorganic hybrid materials that are environmental friendly, have large surface area, and are also expected to be practically used for industrial application the new future and a novel preparation method thereof has been keenly required.

SUMMARY

In this regard, as a result of hard work in order to solve the above problems, the inventors of the present invention found organic-inorganic hybrid materials containing Fe and a preparation method thereof, which is sufficiently manifested by the fast reaction feature of microwaves in the case of performing the crystallization by simply mixing an organic compound in a solvent such as water, organic solvent, etc. in the presence of a mixed-acid comprising nitric acid and hydrofluoric acid during a certain period of time by using Fe which is environmentally friendly instead of using Cr as a metal component, and irradiating microwaves, and thereby completed the present invention. Also, the inventors of the present invention found a novel method for preparing and purifying porous organic-inorganic hybrid materials having a relatively small nano particle size through a environmentally friendly novel preparation method which further comprises the step of purifying by treating the obtained porous organic-inorganic hybrid materials with inorganic salt, wherein hydrofluoric acid is not used at all in some cases when preparing porous organic-inorganic hybrid materials, and the catalytic use of porous organic-inorganic hybrid materials prepared by said method.

According to the first embodiment, the present invention provides a novel method for preparing iron-containing organic-inorganic hybrid materials which was not substantially prepared by conventional preparation methods of Cr-organic-inorganic hybrid materials, and novel iron-containing organic-inorganic hybrid materials having very high porosity and nano-crystalline prepared by said preparation method.

Therefore, it is an object of the present invention to provide high porosity and nano-crystalline iron-containing porous organic-inorganic hybrid materials which were substantially difficult to prepare until now, and a novel preparation method thereof.

According to the present invention, since porous organic-inorganic hybrid materials can be prepared in a short reaction time, energy consumption can be reduced, and thus they are economically and environmentally useful. Also, organic-inorganic hybrid materials can be prepared not only by a batch-type manner but also by a continuous-type manner due to a short reaction time. In addition, porous organic-inorganic hybrid materials can be prepared in a short period of time, and it becomes possible to synthesize organic-inorganic hybrid materials having a unique crystal structure, which was not obtained by conventional electric heating taking a long period of time.

The second embodiment in the present invention provides a novel method for preparing and purifying porous organic-inorganic hybrid materials having a relatively small nano particle size through a environmentally friendly novel preparation method which further comprises the step of purifying by treating the obtained porous organic-inorganic hybrid materials with inorganic salt, wherein hydrofluoric acid is not used at all in some cases when preparing porous organic-inorganic hybrid materials, and provides the catalytic use of porous organic-inorganic hybrid materials prepared by said method. Also, it is an object of the present invention to provide a method for preparing porous organic-inorganic hybrid materials through a quick and continuous-type manner by irradiating microwaves.

The first embodiment of the present invention relates to a novel method for preparing porous organic-inorganic hybrid materials containing Fe, which can be used not only for adsorbents, gas storing materials, sensors, catalysts and catalyst carriers, etc., but also for including guest molecules smaller than the pore size or separating molecules larger than pore size, because porous organic-inorganic hybrid materials have a large surface area and a pore of molecular size or nano size, wherein the organic compound ligand is bonded to a central metal by preparing porous organic-inorganic hybrid materials by irradiating microwaves as a heating source of the hydrothermal or solvothermal synthesis reaction after forming crystal nuclei by a predetermined pre-treatment operation in the presence of iron or iron salt which is the central metal of the porous organic-inorganic hybrid materials, an organic compound which is the ligand bonded to the metal component, a mixed-acid comprising nitric acid and hydrofluoric acid, and a solvent.

That is, the present invention relates to a method for preparing porous organic-inorganic hybrid materials by using iron or iron salt and an organic compound as a reaction raw materials and by heat-treatment in the presence of a solvent, which comprises: pre-treating a reaction solution containing an iron or iron salt, an organic compound, a mixed-acid comprising nitric acid and hydrofluoric acid, and a solvent by stirring the reaction solution in 50~2000 rpm for 5~600 min or by irradiating the reaction solution with supersonic waves of 15,000 Hz~30 MHz for 1~600 min to form crystal nuclei; and preparing organic-inorganic hybrid materials by irradiating the reaction solution in which the crystal nuclei are formed with microwaves of 1~30 GHz at the temperature in the range of 100° C. to 250° C.

The second embodiment of the present invention relates to an efficient method for preparing porous organic-inorganic hybrid materials, characterized by comprising a process of purification in order to increase the surface area of the porous organic-inorganic hybrid materials. In particular, it is characterized by preparing porous organic-inorganic hybrid materials having nano-sized particles without using hydrofluoric acid during hydrothermal synthesis. Also, the present invention relates to the uses characterized by using the porous organic-inorganic hybrid materials obtained by the novel preparation method as a catalyst for an oxidation reaction.

That is, the present invention relates to a method for preparing porous organic-inorganic hybrid materials, which comprises:

(1) Preparing a reaction solution containing a mixture of a metal precursor, an organic compound which may act as a ligand, and a solvent;

(2) heating the reaction solution; and (3) purifying the porous organic-inorganic hybrid materials obtained in the step (2) by treatment with an inorganic salt.

The porous organic-inorganic hybrid materials prepared by said preparation method according to the present invention can be obtained as nanoparticles, and the size of said nano particle is about 450 nm or below. Also, the porous organic-inorganic hybrid materials prepared by said preparation method according to the present invention can be in a form of powder, pellet, thin film or membrane.

In the meantime, electric heating or microwave-irradiation can be used as a way of heating the reaction solution.

The porous organic-inorganic hybrid materials in a form of nanoparticles, thin film or membrane can be easily prepared by methods such as electric heating and irradiating microwaves after immersing the substrate to the mixed reaction solution.

Hereinafter, the present invention will be explained in more detail.

The technical characteristic of the first embodiment of the present invention lies in that microwaves can be applied instead of electric heating which is generally used as a heat source of high temperature reactions. In order to prepare organic-inorganic hybrid materials by such microwaves irradiation, a metal component and organic compound are pre-treated in the presence of a solvent.

Also, while preparing said iron-containing organic-inorganic hybrid materials, the present invention comprises a step for preparing iron-containing organic-inorganic hybrid materials which have excellent crystallinity, reduced the size of crystals, and a large surface area, by using a mixed-acid comprising hydrofluoric acid and nitric acid. That is, the present invention comprises a pre-treating step in which nuclei are formed, and a crystallizing step by using a mixed-acid comprising hydrofluoric acid and nitric acid.

First, the method comprises a pre-treating step in which crystal nuclei are formed by stirring or irradiating supersonic waves in the presence of iron or iron salt as a metal component, an organic compound, a mixed-acid comprising nitric acid and hydrofluoric acid, and a solvent.

Also, a metal component such as iron powder, iron sheet, iron salt, etc. can be used as a component contained in the porous iron-containing organic-inorganic hybrid materials of the present invention.

As an organic compound which may be another component contained in porous organic-inorganic hybrid materials and may act as a ligand, referred to as a linker, any organic compound having a functional group that can coordinate with a metal component presented in the above can be used. For example, functional groups that can coordinate in such organic compound can be —$CO_2^-$, —N, carboxylic acid group, anion group of carboxylic acid, amino group (—$NH_2$), imino group amide group (—$CONH_2$), sulfonic acid group (—$SO_3H$), anion group of sulfonic acid (—$SO_3^-$), methanedithioic acid group (—$CS_2H$), anion group of methanedithioic acid (—$CS_2^-$), pyridine group, pyrazine group, etc.

In order to induce a more stable organic-inorganic hybrid materials, organic compounds having at least two sites for coordination, e.g., being bidentate or tridentate are advantageous. The organic compound may be a neutral organic compound such as bipyridine, pyrazine, etc., anionic organic compounds, e.g., anions of carbonic acid such as terephthalate, naphthalenedicarboxylate, benzenetricarboxylate, glutarate, succinate, etc., and cationic materials, if these have a site for coordination. As for the anions of carbonic acid, in addition to anions having aromatic rings such as terephthalate, any anions, e.g., linear carbonic acid anions such as formate, and anions having non-aromatic rings such as cyclohexyldicarbonate can be used.

Also, in addition to an organic compound having a site for coordination, an organic compound which may be converted to be coordinated in reaction condition due to a potential site for coordination can be used as well. That is, even though organic acids such as terephthalic acid are used, the organic compound such as terephthalate may be bonded to a metal component, after reaction.

Representative examples of the organic compounds which can be used include an organic acid or anion thereof selected from benzenedicarboxylic acid, naphthalenedicarboxylic acid, benzenetricarboxylic acid, naphthalenetricarboxylic acid, pyridinedicarboxylic acid, bipyridyldicarboxylic acid, formic acid, oxalic acid, malonic acid, succinic acid, glutaric acid, hexanedioic acid, heptanedioic acid and cyclohexyldicarboxylic acid, pyrazine, bipyridine, etc. Further, one or more organic compounds can be mixed together to be used.

Said metal component can be mixed with an organic compound in a ratio of 1:0.1~10 (molar ratio). Said ratio can be properly adjusted depending on the kind of the metal component and organic compound.

In addition to a metal component and an organic compound, a suitable solvent is required for preparing porous organic-inorganic hybrid materials. As said solvent, any substance among water, alcohols, ketones and hydrocarbons can be used, and two or more solvents can be mixed together to be used. Preferably, one or a mixture of at least one selected from water, alcohols having 1~10 carbon atoms such as methanol, ethanol, propanol, ketones having 2~10 carbon atoms such as acetone, methylethylketone, and hydrocarbons having 5~20 carbon atoms such as hexane, heptane, octane can be used. More preferably, water can be used.

Also, the present invention is characterized by using acid, preferably, a mixed-acid comprising hydrofluoric acid and nitric acid in order to prepare organic-inorganic hybrid materials. In particular, the iron-containing organic-inorganic hybrid materials of the present invention show a remarkable improvement in crystallinity and decrease in crystal size in comparison with the conventional synthetic methods which uses only hydrofluoric acid. Also, it has been found that the present invention has a remarkable effect that the synthesis can be completed within a couple of minutes. In particular, when a mixed-acid is used, although it has a very short reaction time (within 2 minutes) compared with the case of not using a mixed-acid, it has been confirmed to have an effect such that the crystallinity is improved and the yield is almost the same. Moreover, since it is difficult to prepare organic-inorganic hybrid materials having sufficient crystallinity even if an acid such as acetic acid, sulfuric acid, etc. as other acid, or salt such as ammonium fluoride and sodium chloride, etc. are used, the use of said mixed-acid is another characteristic of the present invention.

The desired iron-containing organic-inorganic hybrid materials of the present invention can be prepared by using nitric acid and hydrofluoric acid in a molar ratio of 0.1~1: 1~0.1 in a mixed-acid. If the molar ratio of nitric acid or hydrofluoric acid deviates from the above range, there are some disadvantages such that the yield is decreased and the reaction time elongated too much.

The pre-treating step is performed by stirring a reaction solution comprising said metal component and organic compound in the presence of a solvent in 50~2000 rpm for 5~600 minutes, or by irradiating the reaction solution with supersonic waves of 15000 Hz~30 MHz for 1~600 minutes. During the pre-treating step, the temperature may raise to a certain extent due to the stirring and the irradiation of supersonic waves. However, it is not preferable if the temperature is raised above the reaction temperature, which it causes the evaporation of the solvent and inclusion of impurities, etc. It is preferable to maintain the pre-treating temperature to 500° C. and below, and more preferable to maintain the temperature to 100° C. and below.

Since the reaction using microwaves is conducted in a very fast rate, in the present invention, the crystallizing step is performed after performing the pre-treating step so as to enhance the uniformity and solubility of the reaction materials and to partly form crystal nuclei.

In case of irradiating microwaves without subjecting to above pre-treating step, the crystallization of organic-inorganic hybrid materials is proceeded slowly, and impurities can be easily included during the reaction.

Said pre-treating step is performed by vigorously stirring, e.g., in 50~2000 rpm, or irradiating microwaves. As for said pre-treating temperature, room temperature (about 20-25° C.) is the preferable temperature range for the crystallization. If the pre-treating temperature is low, the pre-treating effect is weak and thus crystal nuclei are not generated sufficiently. Also, if the pre-treating temperature is high, impurities are easily generated and the pre-treating facility becomes complex.

It is suitable that said pre-treating is conducted for 1 minute~10 hours. If the pre-treating time is short, the pre-treating effect is weak and thus crystal nuclei are not generated sufficiently. Also, if the pre-treating time is long, the pre-treating efficiency becomes low. As for said pre-treating step, irradiating supersonic waves is more efficient since pre-treating time can be decreased, and the reaction materials can be formed more uniformly.

In case of performing the pre-treating step by stirring, it is preferable to stir the metal component and the organic compound in the presence of a solvent in 50~2000 rpm for 5~600 minutes, and in case of performing the pre-treating step by irradiating supersonic waves, it is more preferable to irradiate supersonic waves of 15000 Hz~30 MHz for 1~600 minutes.

After performing the pre-treating step as above, the crystallizing step to form organic-inorganic hybrid materials by irradiating microwaves to the reaction solution in which the crystal nuclei are formed is performed.

In said crystallizing step, microwaves of 1~30 GHz can be irradiated. Preferably, using microwaves of a frequency of 2.54 GHz, which is used generally in industries.

In said crystallizing step, the reaction temperature is not substantially limited. However, the reaction can be performed in the range of 100~250° C., preferably in the range of 150~220° C. In this regard, if said reaction temperature is below 100° C., the crystallization rate is slow and thus not efficient, and if the reaction temperature exceeds 250° C., materials having no pores can be easily obtained and the reaction rate becomes too fast so that impurities can be easily included, and the inner pressure of the reactor becomes higher, which makes the constitution of the reactor not economic.

The pressure within the reactor while performing said crystallization is not substantially limited. However, it is simple to synthesize the materials at autogeneous pressure of the reaction materials at the reaction temperature. Also, the reaction may be performed at high pressure by adding inert gas such as nitrogen, helium.

As stated above, the present invention comprising a pre-treating step and a crystallizing step can be performed both in the batch-type manner and in the continuous-type manner unlike methods using the conventional electric heating.

The batch-type reactor has a low productivity per hour, and thus is suitable for producing a small amount of porous organic-inorganic hybrid materials. The continuous-type reactor needs a large amount of investment cost, but is suitable for mass-production. As for the batch-type reactor, a reaction time of 1 minute~8 hours, preferably, 1 minute~1 hour, is suitable. If the reaction time is too long, impurities can be easily included. As for the continuous-type reactor, a residence time of 1 minute~1 hour, preferably, 1 minute~20 minutes, is suitable. However, if the residence time is too long, the productivity is low, and if the residence time is too short, the conversion rate of the reaction is low.

In case of using a batch-type reactor, the reaction material may be stirred during the reaction, and a stirring rate of 50~2000 rpm is suitable. However, the reaction may be performed without the stirring process, which makes the constitution and operation of the reactor simple and easy for application.

According to the present invention as described above, porous organic-inorganic hybrid materials containing Fe which have features such as large surface area, crystalline structure of a very high regularity and relatively high thermal stability, etc. can be prepared within a short period of time. Also, because the crystallization time has been remarkably reduced, porous organic-inorganic hybrid materials having a crystal structure which was not obtained by applying the conventional electric heating can be prepared. In particular, as for the porous organic-inorganic hybrid materials containing iron prepared by mixed-acid, the crystal size of the porous organic-inorganic hybrid materials is reduced by ⅙ or below, and thus the surface area has increased by at least 15%.

In the second embodiment of the present invention, the method for preparing porous organic-inorganic hybrid materials of the present invention is for increasing the surface area of the porous organic-inorganic hybrid materials, which is characterized by further comprising a step of purifying impurities within the pore of the organic-inorganic hybrid materials by treating them using inorganic salts such as ammonium chloride or potassium fluoride, etc. in addition to a generally used solvent. In particular, it is possible to provide an environmentally friendly preparation method because organic-inorganic hybrid materials having a particle size of nano size can be prepared without using hydrofluoric acid in the hydrothermal synthesis for preparing nanoporous materials. Also, said porous organic-inorganic hybrid materials are characterized by having the use of being applied as a catalyst for oxidation reaction.

In said preparation method, as a metal component, which is one of components contained in porous organic-inorganic hybrid materials, any metal can be used. The representative metal components include Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Mg, Ca, Sr, Ba, Sc, Y, Ga, In, Tl, Si, Ge, Sn, Pb, As, Sb, Bi, etc. In particular, transition metals which easily form a coordination compound are suitable. Among said transition metals, chromium, vanadium, iron, nickel, cobalt, copper, titanium and manganese, etc. are suitable, and chromium and iron are the most suitable one. In addition to transition metals, representative elements forming a coordination compound and metals such as lanthanide can also be used. Among elements, aluminum and silicon are suitable, and among lanthanide metals, cerium and lanthanum are suitable. As a metal source, metal itself, and any compound of metal can be used.

In the second embodiment of the present invention, the organic compound which may be another component contained in the organic-inorganic hybrid materials and may act as a ligand, and the solvent used in the synthesis of the organic-inorganic hybrid materials are the same as those used in the first embodiment.

In order to regulate the crystal growth rate of the nanoporous organic-inorganic hybrid materials, an acid, in particular, a mixed-acid comprising hydrofluoric acid along with nitric acid, hydrochloric acid and hydrofluoric acid can be used.

Meanwhile, in the process using hydrofluoric acid, there may be a limitation in using reactors other than the Teflon reactor. Until now, for the crystal growth rate of the nanoporous organic-inorganic hybrid materials, it is well known that the nuclei formation rate is low, while the crystal growth rate is relatively high. Therefore, in reaction materials including hydrofluoric acid, the nuclei formation rate becomes relatively slow due to the strong bonding characteristics between metal ion and fluoride ion, and thus it may be difficult to obtain nanoporous materials having a small crystal size.

Therefore, in the second embodiment of the present invention, the method for preparing porous organic-inorganic hybrid materials of the present invention is characterized by using an inorganic acid except hydrofluoric acid for preparing porous organic-inorganic hybrid materials, in order to solve the above problems caused by using hydrofluoric acid. Thereby, nanoporous organic-inorganic hybrid materials having a relatively small nano particle size can be prepared by said preparation method of the present invention without using hydrofluoric acid at all.

Also, in order to remove the metal or organic ligand present as impurities within the pores of the porous organic-inorganic hybrid materials prepared by the second embodiment of the present invention, impurities were conventionally removed using a solvent. However, as for such case, there is a limitation in removing organic or inorganic impurities chelated within the pore. In comparison with the above, in the preparation method of the present invention, impurities within the pore of nanoporous organic-inorganic hybrid materials can be efficiently removed by treating porous organic-inorganic hybrid materials using an inorganic salt, in particular, comprising monovalent or divalent cation selected from the group consisting of $NH^+_4$, alkali metal and alkali earth metal, and monovalent or divalent anion selected from the group consisting of halogen anion, carbonic acid ion ($CO_3^{2-}$), nitric acid ion and sulfuric acid ion. Accordingly, nanoporous organic-inorganic hybrid materials having large surface area can be obtained as surface area of porous organic-inorganic hybrid material increases after the purifying process using said inorganic salt. At least one inorganic salt selected from the group consisting of a salt comprising $Ca^{2+}$ or $Mg^{2+}$ as divalent cation and $F^-$, $I^-$ or $Br^-$ as monovalent anion, a salt comprising monovalent cation and divalent anion, $NH_4F$, $KF$, $KI$ and $KBr$ can be used as said inorganic salt. In particular, inorganic salt such as ammonium chloride or potassium fluoride, etc. can be used.

In the present invention, it has been confirmed by measuring the surface area that the nitrogen adsorption amount of the nanoporous organic-inorganic hybrid materials after being treated with inorganic salt increases by 200 ml/g.

In the present invention, the reaction temperature for preparing porous organic-inorganic hybrid materials is not substantially limited. However, a temperature of at least 100° C. is suitable. A temperature of 100° C.~250° C. is preferable, and a temperature of 150° C.~220° C. is more preferable. If the reaction temperature is too low, the reaction rate is slow and thus not efficient, and if the reaction temperature is too high, materials having no pore can be easily obtained and the reaction rate becomes too high so that impurities can be easily included. Also, the inner pressure of the reactor becomes higher, and thus the constitution of the reactor is not economic. Although the reactor pressure is not substantially limited, it is convenient to synthesize the materials at autogeneous pressure of the reaction materials at reaction temperature. Also, the reaction may be performed at high pressure by adding inert gas such as nitrogen, helium.

In addition to the hydrothermal synthetic using the electric heating, hydrothermal synthesis in a batch-type manner or continuous-type manner with irradiating microwaves can be used. Also, the membrane or thin film of the organic-inorganic hybrid materials can be prepared by irradiating microwaves to heat after immersing the substrate to the mixed solution of the reaction materials from said step 1).

According to the preparation method of the present invention, in particular, a novel porous organic-inorganic hybrid material which does not contain fluorine can be obtained comprising a compound represented by formula of $M_3OH(H_2O)_2O[C_6H_4(CO_2)_2]_3$ (M is one metal selected from the group consisting of Fe, Cr, V and Al) and/or a hydrate thereof. Also, a novel porous organic-inorganic hybrid material which does not contain fluorine can be obtained comprising a compound represented by formula of $M_3O(H_2O)_2OH[C_6H_3—(CO_2)_3]_2$ (M is one metal selected from the group consisting of Fe, Cr, V and Al) and/or a hydrate thereof.

Also, the porous organic-inorganic hybrid materials obtained by the preparation method of the present invention can be used as a catalyst for oxidation reaction or as an acid catalyst. In case the porous organic-inorganic hybrid materials obtained by the preparation method of the present invention are used as a catalyst for oxidation reaction, the catalyst shows activity for oxidation reactions such as sulfoxidation reaction, epoxidation reaction, phospine oxidation reaction or Fridel-Crafts benzylation reaction, etc. In case the porous organic-inorganic hybrid materials obtained by the preparation method of the present invention are used as an acidic catalyst, the catalyst shows activity for acid-catalystic reactions such as alkylation reaction, esterification reaction or Beckman rearrangement reaction, etc.

As stated above, the present invention in which the crystallizing step is performed by using microwaves as a heat source after performing the pre-treating step to form crystal nuclei by stirring the mixture comprising a metal component, an organic compound, a mixed-acid comprising nitric acid and hydrofluoric acid, and a solvent and irradiating the microwaves in advance before the step of crystallizing the porous organic-inorganic hybrid materials, and the preparation time of porous organic-inorganic hybrid materials can be remarkably reduced, and the reactor capacity can be reduced. Also, porous organic-inorganic hybrid materials containing iron can be prepared using environmentally and economically advantageous methods such as the continuous-type process.

Also, porous organic-inorganic hybrid materials containing iron of a crystal structure, which could not be obtained by the conventional electric heating requiring a longer period of time, can be selectively synthesized because the reaction time has been reduced as stated above. The prepared porous organic-inorganic hybrid materials as described above can be widely applied in various aspects such as for the preparation of catalysts, catalyst carriers, adsorbents, gas storing materials, ion exchanging materials, and nanoreactors, and nanomaterials, etc.

In another aspect, although the porous organic-inorganic hybrid materials prepared according to the novel preparation method of the present invention do not use hydrofluoric acid during the hydrothermal synthesis, they are nanoporous materials having high crystallinity. In particular, their surface area can be increased by purifying them by removing the impurities within the pore of the nanoporous organic-inorganic hybrid materials by treating them with an inorganic salt.

Also, the nanoporous organic-inorganic hybrid materials prepared in accordance with the preparation method of the present invention can be used as a selective catalyst for oxidation reactions or an acidic catalyst. Such organic-inorganic hybrid materials can be used for the preparation of other catalysts, catalyst carriers, adsorbents, gas storing materials, ion exchanging materials, nanoreactors and nanomaterials. In particular, the nanoparticles of said organic-inorganic hybrid materials can be used as catalysts having excellent activity, sensors, optoelectronic materials and materials for medical use.

Hereinafter, the present invention will be explained in more detail with reference to examples, but not limited thereto.

DETAILED DESCRIPTION

Examples

Example 1

Preparation of Porous Organic-Inorganic Hybrid Material (Fe-BTC) Using a Mixed-Acid After adding metallic iron 1 mmol, 1M $HNO_3$ 60 ml, 5M HF (aqueous solution) 40 ml and 1,3,5-benzenetricarboxylic acid (BTCA) 7 mmol to a Teflon reactor, distilled water was added. The final molar ratio of the reaction material was Fe:HF:$HNO_3$:BTCA:$H_2O$=1:2:0.6:0.7:278.

The mixed reaction material was stirred in 500 rpm for 20 minutes at room temperature to make the reaction material as homogeneous as possible.

After mounting the Teflon reactor containing said pre-treated reaction material on a microwaves reactor (CEM company, model Mars-5) and then raising the temperature to 200° C. by irradiating microwaves (2.54 GHz), crystallization was performed by maintaining the reaction material at 200° C. for 2 minutes. Then, the reaction material was cooled to room temperature, centrifuged, washed with distilled water and dried to obtain a porous organic-inorganic hybrid material (Fe-BTC; Fe-benzenetricarboxylate).

Figure 1:
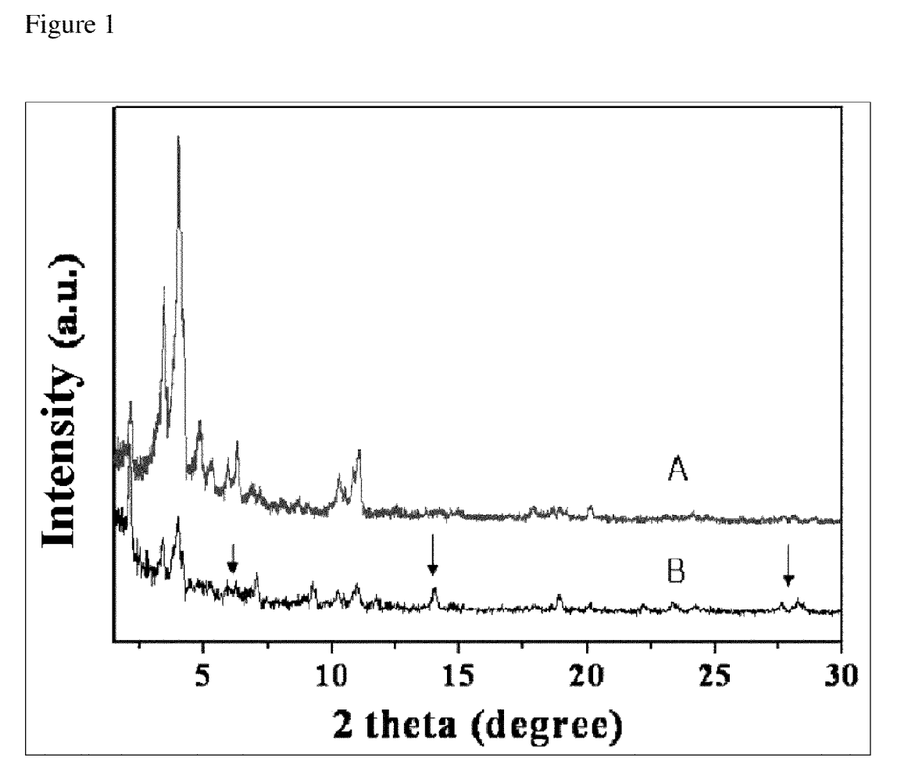
FIG. 1 is an X-ray diffraction patterns of iron benzenetricarboxylate organic-inorganic hybrid materials: (A) is an X-ray diffraction pattern of the organic-inorganic hybrid material obtained by Example 1, and (B) is an X-ray diffraction pattern of the organic-inorganic hybrid material obtained by Comparative Example 1.
Figure 2:
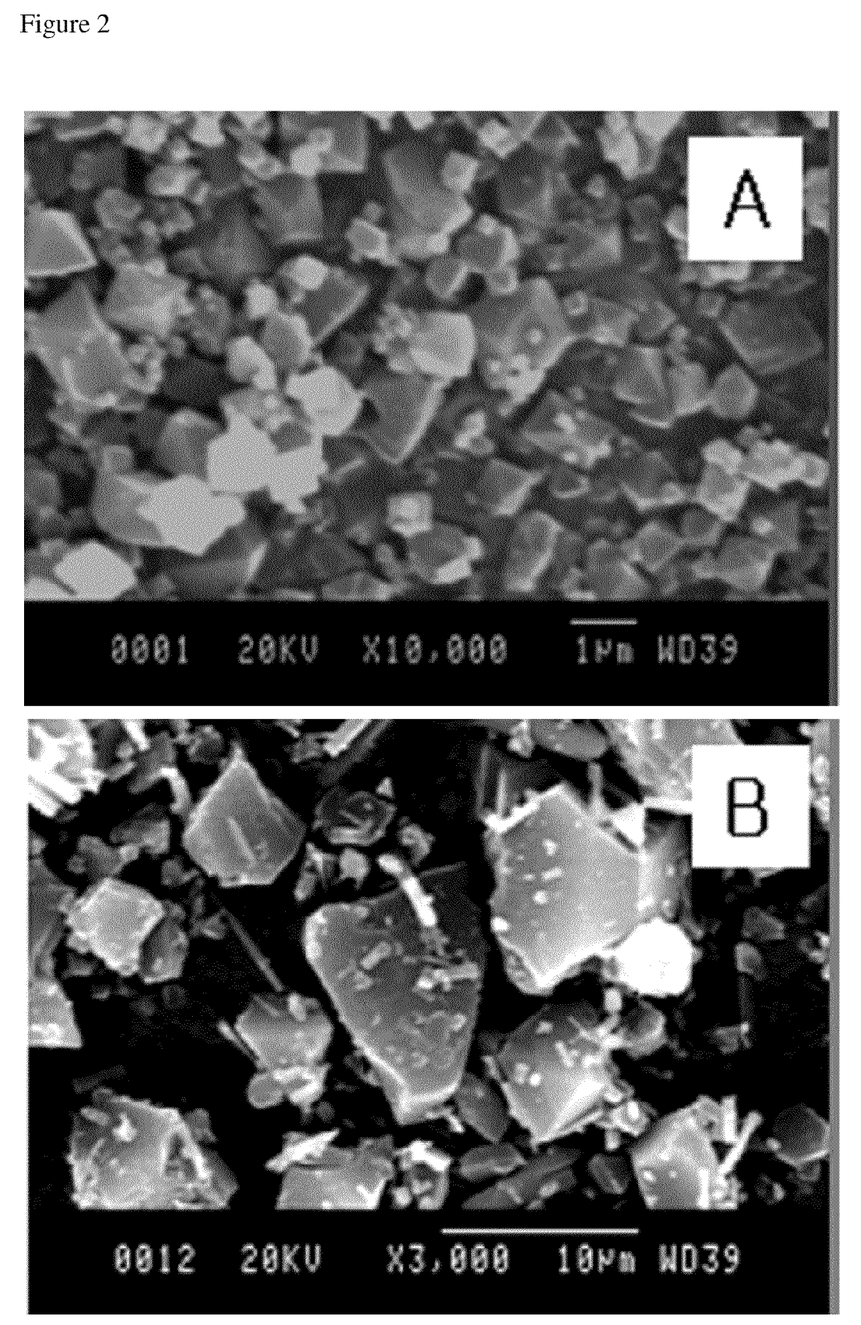
FIG. 2 is an electron microscope image of iron benzenetricarboxylate organic-inorganic hybrid materials: (A) is an electron microscope image of the organic-inorganic hybrid material obtained by Example 1, and (B) is an electron microscope image of the organic-inorganic hybrid material obtained by Comparative Example 1.
Figure 3:
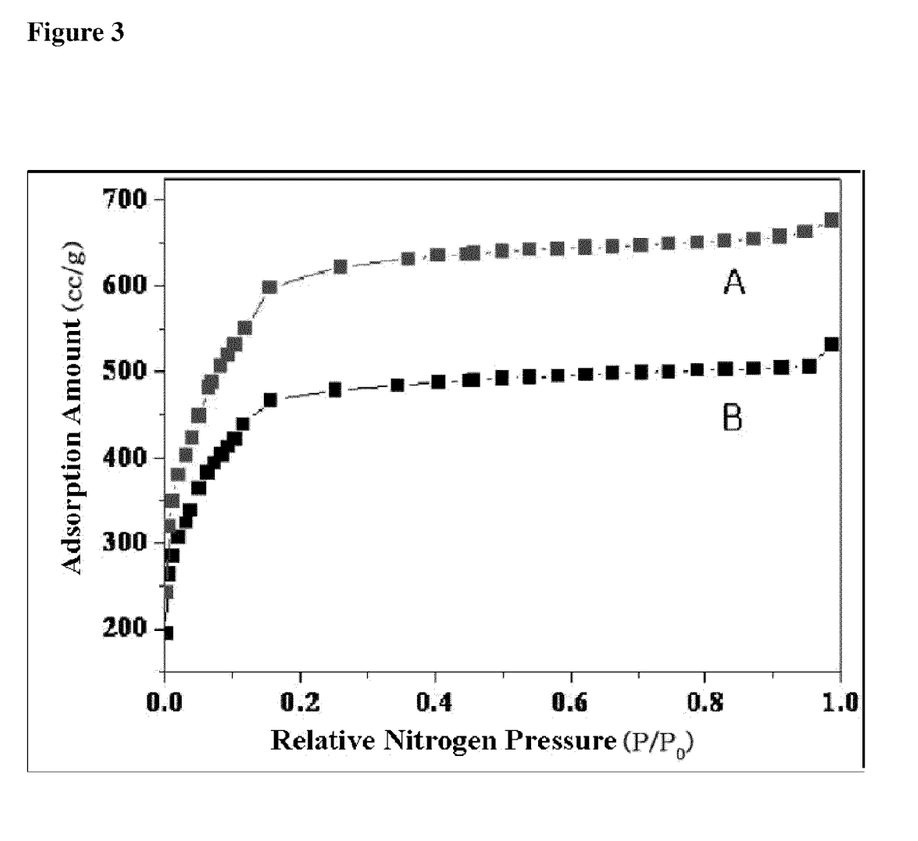
FIG. 3 is graphs illustrating the experimental results of nitrogen adsorption of iron benzenetricarboxylate organic-inorganic hybrid materials: (A) is the result for Example 1, and (B) is the result for Comparative Example 1.

The X-ray diffraction pattern of the solid phase porous organic-inorganic hybrid material obtained as above is as shown in A of FIG. 1. As a result of elementary analysis, it showed a molar ratio of Fe:C:F=1:6.5:0.32, and as a result of a nitrogen adsorption experiment, it had a BET surface area of 2,050 $m^2/g$ and a pore volume of 1.0 cc/g. And it formed as porous particles with yield of 96%. The relative intensity of the first three XRD peaks of FIG. 1 are very strong in the organic-inorganic hybrid material synthesized using a mixed-acid. From the above, it can be found that the crystallinity is improved. Also, compared with Comparative Example 1 (FIG. 1b), the reaction time was decreased 30 times, and the yield was almost the same. In particular, the crystal size confirmed by an electron microscope was reduced by ⅙ in comparison with the hybrid material synthesized using a single acid (see A of FIG. 2). As for Comparative Example 1, which was a synthesized using a single acid, the surface area was reduced due to non-porous impurities (see B of FIG. 3; surface area 1,590 $m^2/g$).

The above results show that the material has a crystal structure similar to the Cr-MIL-100 structure, which has been previously published [Bulletin of Korean Chemical Society vol. 26, p. 880 (2005)].

From above results it can be known that porous organic-inorganic hybrid materials can be obtained very efficiently in a very short period of time, by preparing porous organic-inorganic hybrid materials through performing pre-treating of the reaction material and then irradiating microwaves.

Comparative Example 1

Preparation of Porous Organic-Inorganic Hybrid Materials (Fe-BTC) Using a Single Acid A porous organic-inorganic hybrid material was prepared by the same method as Example 1, except that the hybrid material was prepared using a single acid which is not a nitric acid. After adding metallic iron 1 mmol, 5M HF (aqueous solution) 40 ml and 1,3,5-benzenetricarboxylic acid (BTCA) 7 mmol to a Teflon reactor, distilled water was added. The final molar ratio of the reaction material was Fe:HF:BTCA:$H_2O$=1:2:0.6:278. The temperature of microwave irradiation to the organic-inorganic hybrid material was 200° C., and the reaction was carried out for an hour. The yield of the solid phase porous organic-inorganic hybrid material obtained was 82%. The X-ray diffraction shape and adsorption feature of the porous organic-inorganic hybrid material were very similar to the results as in Example 1. However, it can be known that the overall peak intensity was low, the surface area was reduced by 15% due to non-porous impurities and large particle size (see B of FIG. 3), and the reaction time increased 30 times compared with Example 1.

Example 2

Cr-BDC-1

Figure 4:
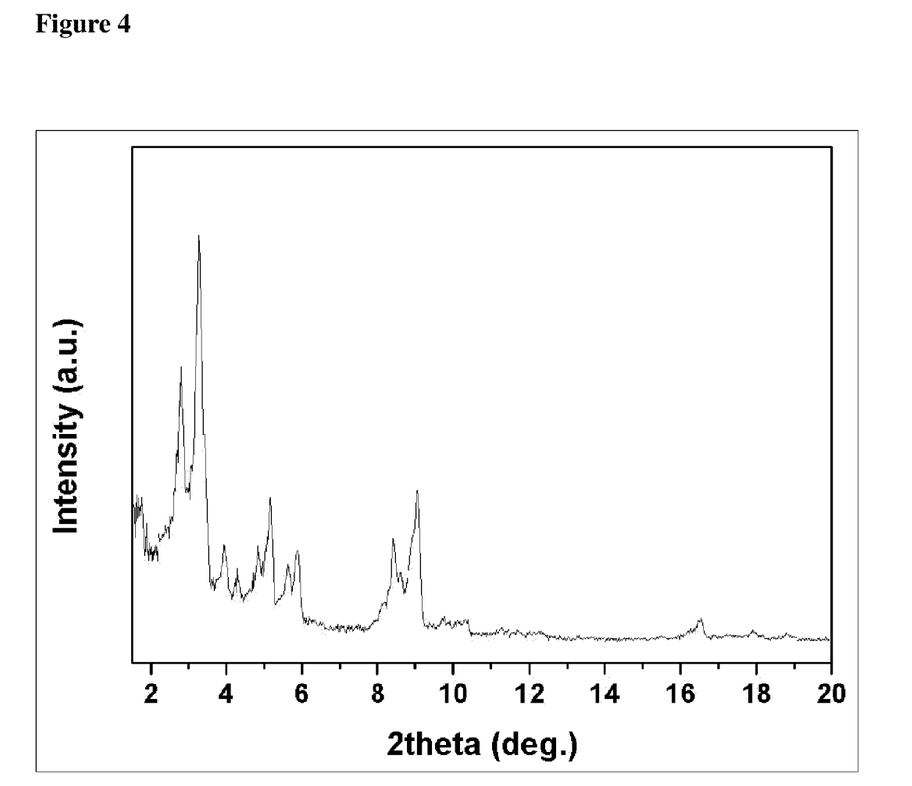
FIG. 4 is an X-ray diffraction pattern of the chromium-terephthalate, which is a porous organic-inorganic hybrid material prepared in accordance with the preparation method of Example 2 of the present invention.

After adding $Cr(NO_3)_3 \cdot 9H_2O$, and 1,4-benzenedicarboxylic acid (BDCA) to a Teflon reactor, distilled water was added so that the final molar ratio of the reaction material was $Cr:HNO_3:BDCA:H_2O=1:0.1:1:272$. Basically, if $Cr(NO_3)_3$ dissolves in water, it is hydrated to become a strong acid. Thus, it has the same effect as adding $HNO_3$. After putting the Teflon reactor containing said reaction material in an electric oven and reacting it for 11 hours at 210° C., it was cooled to room temperature, centrifuged, washed with distilled water and dried to obtain chromiumterephthalate (Cr-BDC) as a porous organic-inorganic hybrid material. The result of the X-ray diffraction analysis of the thus prepared Cr-BDC showed characteristic diffraction peaks of $2\theta$ values at about 3.3, 5.2, 5.9, 8.5 and 9.1, and it can be known that the chromiumterephthalate having cubic crystallinity was obtained (FIG. 4). It has been confirmed that the XRD pattern of the chromiumterephthalate crystal obtained from the present example was consistent with the values published in prior art [Science 23, 2040, 2005]. Thus, it can be shown that the porous organic-inorganic hybrid materials can be obtained very efficiently by an environmentally friendly process that does not use hydrofluoric acid (HF) in the reaction materials. As a result of ICP analysis, it can be shown that the chromiumterephthalate, which is a porous organic-inorganic hybrid material obtained, does not contain F, and thus its structure is the same as MIL-101 but it does not include F in its structure, thus being materials that can be represented by formula of $Cr_3OH(H_2O)_2O[C_6H_4(CO_2)_2]_3 \cdot nH_2O$ (n~25).

Example 3

Cr-BDC-2

Figure 5:
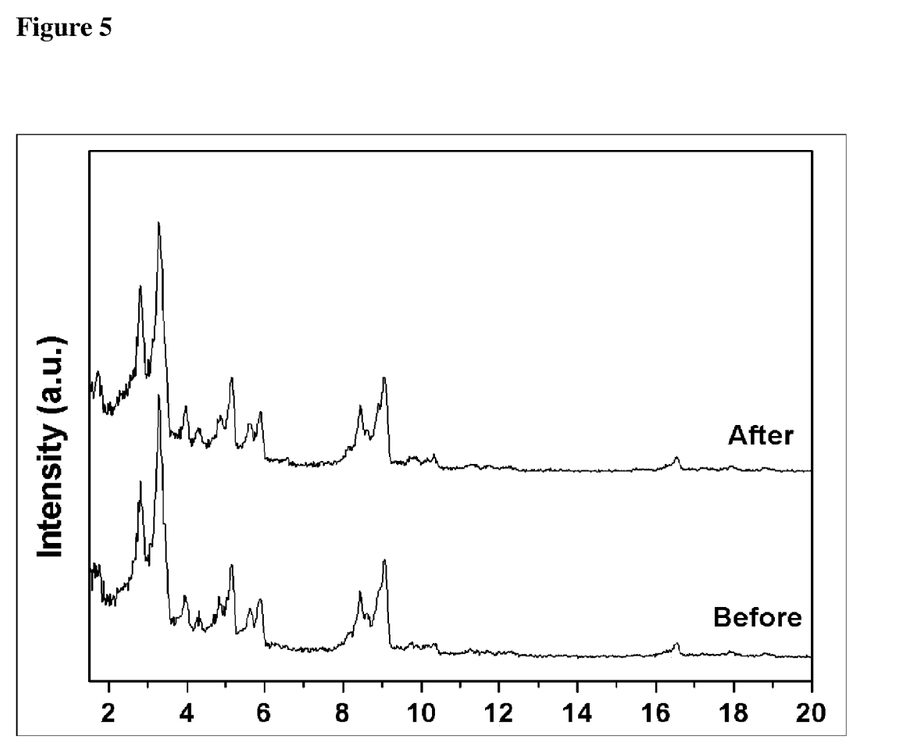
FIG. 5 is the result of X-ray diffraction pattern before and after purifying the chromiumterephthalate which is the porous organic-inorganic hybrid material prepared in accordance with the purifying method of Example 2 of the present invention, wherein (a) is the spectrum before purifying, and (b) is the spectrum after purifying.
Figure 6:
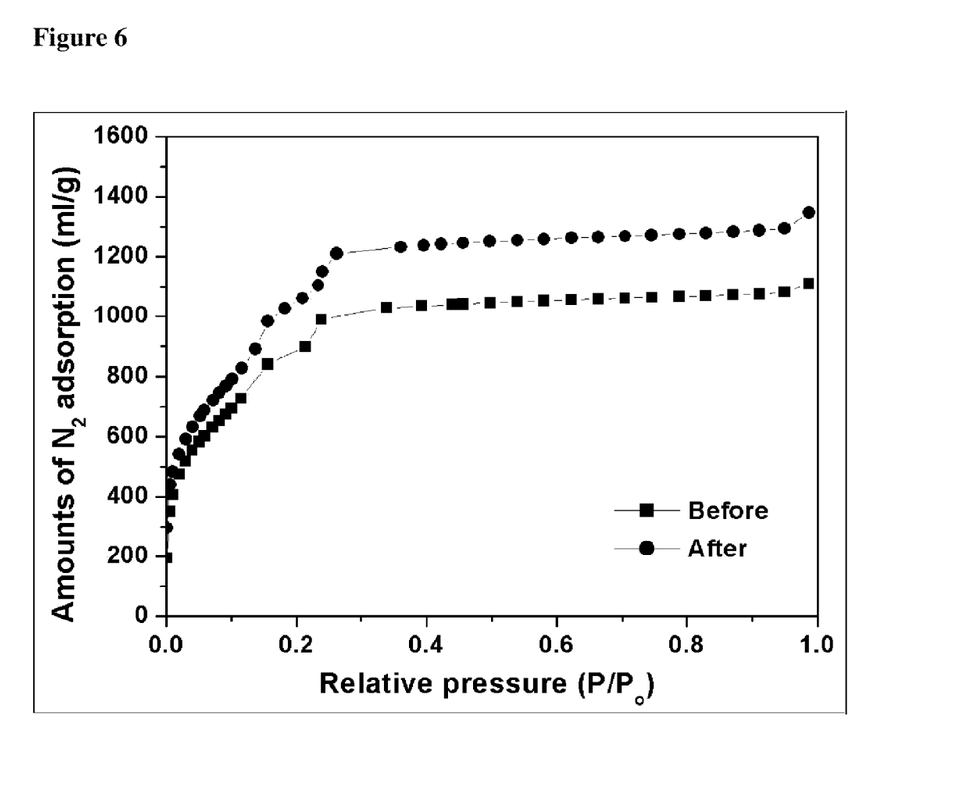
FIG. 6 is an isotherm result of nitrogen adsorption of the chromium terephthalate which is the porous organic-inorganic hybrid material obtained by Example 3 of the present invention.

Organic-inorganic hybrid materials with improved surface area were prepared by removing impurities present in pores of the porous materials by putting the porous organic-inorganic hybrid materials 1 g prepared in Example 2 in 50 ml of 1M $NH_4F$ and stirring it at 70° C. From the X-ray diffraction spectrum (FIG. 5), it can be confirmed that its crystallinity was maintained without being damaged after treating with ammonium fluoride. Also, from the result of measuring the nitrogen adsorption of the porous organic-inorganic hybrid material before and after treating with ammonium fluoride, it can be shown that organic-inorganic hybrid materials having features such that the surface area increases by 700 $m^2/g$ (before treating with ammonium fluoride, 3373 $m^2/g \rightarrow$ after treatment, 4074 $m^2/g$) due to the ammonium fluoride treatment, and the adsorption amount at $P/Po=0.5$ increases by 200 ml/g (before treating with ammonium fluoride, 1050 ml/g$\rightarrow$after treatment, 1250 ml/g) can be obtained (FIG. 6).

Example 4

Figure 7:
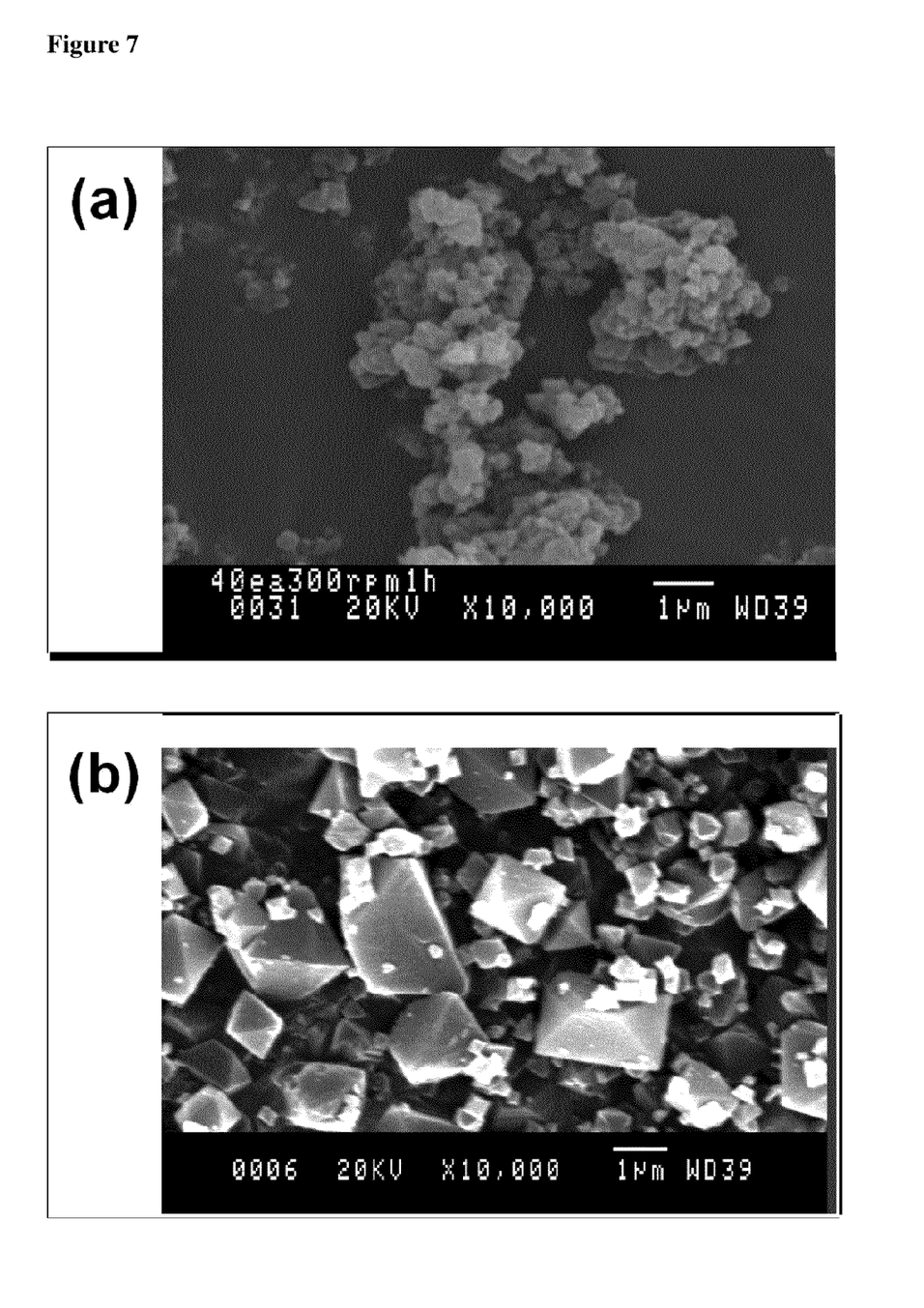
FIG. 7 is electron microscope images of the chromium terephthalate which is the porous organic-inorganic hybrid materials obtained by Example 4(a) and Comparative Example 3(b) of the present invention.

Preparation of Porous Organic-Inorganic Hybrid Material (Fe-BTC-1) by Microwaves Irradiation After adding metallic iron 1 mmol, 1M $HNO_3$ 60 ml and 1,3,5-benzenetricarboxylic acid (BTCA) 7 mmol to a Teflon reactor, distilled water was added. The final molar ratio of the reaction material was $Fe:HNO_3:BTCA:H_2O=1:0.6:0.7:278$. The reaction material was stirred in 500 rpm for 20 minutes at room temperature, to make reaction material homogeneous. After mounting the Teflon reactor containing said pre-treated reaction material on a microwaves reactor (CEM company, model Mars-5) and raising the temperature to 200° C. by irradiating microwaves (2.54 GHz), crystallization was performed by maintaining the reaction mixture at 200° C. for 2 minutes. Then, the reaction mixture was cooled to room temperature, centrifuged, washed with distilled water and dried to obtain the us organic-inorganic hybrid material (Fe-BTC). It is shown that the shape of the X-ray diffraction spectrum was similar to that of the Cr-MIL-100 structure which is the crystal structure previously published [Bulletin of Korean Chemical Society vol. 26, p. 880 (2005)]. As a result of ICP analysis, it can be known that the chromiumterephthalate, which is a porous organic-inorganic hybrid material obtained, does not contain F, and thus its structure is the same as MIL-100, but it does not include F within its structure, and it is materials that can be represented by formula of $Fe_3O$ $(H_2O)_2$ $OH[C_6H_3—(CO_2)_3]_2 \cdot nH_2O$ (n~14.5). As a result of electron microscope analysis, it can be shown that its particle size was reduced to at most 200~500 nm (FIG. 7a).

Example 5

Preparation of Porous Organic-Inorganic Hybrid Material (Fe-BTC-2) by Electric Heating A porous organic-inorganic hybrid material was prepared in the same method as Example 4 except that the organic-inorganic hybrid material was prepared by heating for 6 hours by an electric heating using the conventional electric heating instead of irradiating microwaves as a heat source. As a result of XRD analysis, it can be confirmed that relative intensity of the peak was different; however, a diffraction pattern was shown in the same position as Example 4 as for the crystal structure of the organic-inorganic hybrid material prepared as above. As a result of analysis using an electron microscope, a relatively large crystal whose particle size is 2-5 μm was obtained.

Example 6

Cr-BDC-3

An organic-inorganic hybrid material was prepared in the same method as Example 2 except that heating by microwaves irradiation was used instead of the electric heating in Example 2. However, the organic-inorganic hybrid material was prepared by using microwaves reaction device of 2.5 GHz and maintaining the reaction temperature at 210° C. for 40 minutes. The X-ray diffraction pattern analysis showed that this material is having the same structure as in Example 2.

Example 7

Fe-BDC-3

An organic-inorganic hybrid material was prepared in the same manner as in Example 2 except that Fe was used instead of $Cr(NO_3)_3 \cdot 9H_2O$. It can be known from the X-ray diffraction pattern that the material having the same structure as in Example 1 was obtained.

Example 8

V-BDC-1

An organic-inorganic hybrid material was prepared in the same manner as in Example 2 except that VCl₃ was used instead of Cr(NO₃)₃.9H₂O as in Example 2. The X-ray diffraction spectrum show that the material having the same structure as in Example 2 was obtained. The electron microscope photograph shows that the organic-inorganic hybrid material having uniform particle size of 50-80 nm was obtained.

Example 9

Cr-BDC-1 Thin Film

After adding Cr(NO₃)₃.9H₂O, and 1,4-benzenedicarboxylic acid (BDCA) to a Teflon reactor, distilled water was added so that the final molar ratio of the reaction material was Cr:BDCA:H₂O=1:1:275. The Teflon reactor containing a reaction material and an alumina substrate wherein the alumina substrate is perpendicularly aligned in the solution was placed into a microwaves reactor (CEM company, model Mars-5), and the temperature was raised to 210° C. over 3 minutes by irradiating microwaves of 2.54 GHz. After the reaction was conducted at 210° C. for 30 minutes, the reaction mixture was cooled to room temperature, centrifuged, washed with distilled water and dried to obtain an organic-inorganic hybrid material, Cr-BTC. The X-ray diffraction spectrum of the obtained thin film was consistent with the result of as in Example 2. The electron microscope photograph of the crystal of the thin film of the organic-inorganic hybrid material obtained as above is shown in FIG. 7, which shows the Cr-BDC/alumina thin film is coated with very uniform particles. Accordingly, it can be confirmed that the preparation method of the present invention is a very efficient method by which thin films of organic-inorganic hybrid materials can be directly prepared using microwaves irradiation. (the same as in Example 2)

Example 10

Fe-BTC-1 Catalytic Reaction

Figure 8:
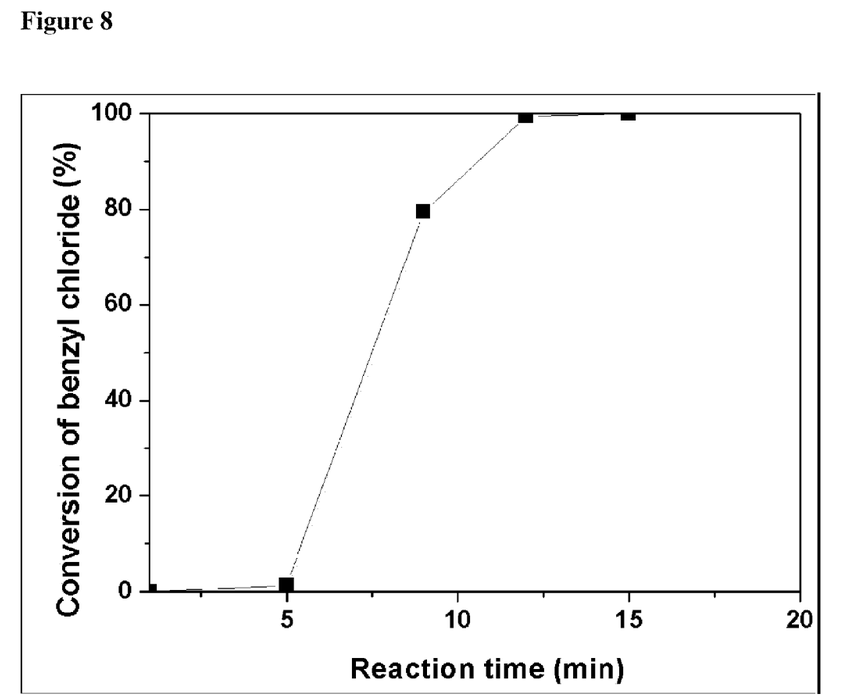
FIG. 8 is the result of the Fridel-Crafts benzylation reaction using the porous organic-inorganic hybrid material obtained by Example 10 of the present invention as a catalyst.

In order to use the nanoporous organic-inorganic materials obtained by the preparation method of the present invention as a catalyst for the Fridel-Crafts benzylation reaction, the Fridel-Crafts benzylation reaction was performed at 70° C. by mixing the nanoporous organic-inorganic material, Fe-BTC 0.1 g, obtained from Example 5, with benzene (7.8 ml) and benzyl chloride (1.3 ml). As a result, it has been confirmed that the nanoporous organic-inorganic hybrid materials of the present invention have very high activity as a catalyst to enable the reaction to be completed 100% within 10 minutes (FIG. 8).

Example 11

Fe-BTC-1 Catalytic Reaction

As a result of reacting thioanisole with hydrogen peroxide at room temperature using the organic-inorganic hybrid material, Fe-BTC 0.1 g, obtained in Example 5, as a catalyst, it has been confirmed that the Fe-BTC has very high oxidation catalyst activity showing conversion rate of 88% and selectivity of 100%.

Comparative Example 2

Cr-BDC-4

A nanoporous organic-inorganic hybrid material was prepared using hydrofluoric acid for preparing a reaction mixture in the preparation method as in Example 2. The final molar ratio of the reaction mixture was Cr:HF:BDCA:H₂O=1:1:1: 272. A result of analyzing the surface area of the nanoporous organic-inorganic hybrid material prepared as above shows that the organic-inorganic hybrid material has adsorption amount of 1044 ml/g and BET surface area of 3439 m²/g at P/Po=0.5.

Comparative Example 3

Fe-BTC

A nanoporous organic-inorganic hybrid material was prepared using hydrofluoric acid for preparing a reaction mixture in the preparation method as in Example 4. The final molar ratio of the reaction mixture was Fe:HF:HNO₃:BTCA: H₂O=1:1:0.6:0.7:278. As a result of X-ray diffraction analysis of the organic-inorganic hybrid material prepared as above, it can be known that the material having very large crystal size (1~5 μm) was obtained instead of a organic-inorganic hybrid material having the same crystallinity as in Example 4 (FIG. 7*b*).

From the results of the examples and comparative examples above, in comparison with the method using hydrofluoric acid, it has been confirmed that nanoporous organic-inorganic hybrid materials having the same crystallinity were prepared by the preparation method that does not use hydrofluoric acid. In particular, it has been confirmed that the surface area increases by at least 10% when treated with inorganic salt such as ammonium salt and potassium fluoride, etc. Also, it has been confirmed that the nanoporous organic-inorganic hybrid materials prepared in accordance with the preparation method of the present invention have very high activity as a catalyst.

The invention claimed is:

1. A method for preparing porous organic-inorganic hybrid materials, which comprises:
    (1) preparing a reaction solution containing a mixture of a metal precursor, an organic compound which acts as a ligand and a solvent;
    (2) heating the reaction solution; and
    (3) purifying the porous organic-inorganic hybrid materials obtained in the step (2) by treatment with an inorganic salt.

2. The method as set forth in claim 1, wherein the reaction solution in the step (1) further comprises an inorganic acid except for hydrofluoric acid.

3. The method as set forth in claim 1, wherein the reaction solution in the step (2) is heated with electricity or microwave-irradiation.

4. The method as set forth in claim 1, wherein the inorganic salt used in the step (3) comprises a monovalent or divalent cation selected from the group consisting of $NH^+_4$, alkali metals and alkali earth metals, and a monovalent or divalent anion selected from the group consisting of halogen anions, carbonate anion ($CO_3^{2-}$), nitrate ion and sulfate ion, and impurities in the obtained porous organic-inorganic hybrid materials are purified by treating the porous organic-inorganic hybrid materials with said inorganic salt.

5. The method as set forth in claim 1, wherein the metal precursor is at least one metal or compound thereof selected from the group consisting of Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Mg, Ca, Sr, Ba, Sc, Y, Al, Ga, In, Tl, Si, Ge, Sn, Pb, As, Sb and Bi.

6. The method as set forth in claim 1, wherein the solvent contained in the reaction solution is a mixture of at least one selected from the group consisting of water, alcohols having 1~10 carbon atoms, ketones having 2~10 carbon atoms and hydrocarbons having 5~20 carbon atoms.

7. The method as set forth in claim 1, wherein the organic compound which acts as a ligand is a compound containing at least one functional group selected from the group consisting of carboxylic acid group, anion group of carboxylic acid, amino group (—NH$_2$), imino group amide group, sulfonic acid group (—SO$_3$H), anion group of sulfonic acid (—SO$_3^-$), methanedithioic acid group (—CS$_2$H), anion group of methanedithioic acid group (—CS$_2^-$), pyridine group and pyrazine group, or a mixture thereof.

8. The method as set forth in claim 7, wherein the compound containing anion group of carboxylic acid is derived from a compound selected from the group consisting of benzenedicarboxylic acid, naphthalenedicarboxylic acid, benzenetricarboxylic acid, naphthalenetricarboxylic acid, pyridinedicarboxylic acid, bipyridyldicarboxylic acid, formic acid, oxalic acid, malonic acid, succinic acid, glutaric acid, hexanedioic acid, heptanedioic acid and cyclohexyldicarboxylic acid.

9. The method as set forth in claim 1, wherein the metal precursor is one metal selected from the group consisting of Cr, Fe and V and the organic compound which acts as a ligand is benzenedicarboxylic acid.

10. The method as set forth in claim 2, wherein the reaction solution which comprises an iron or iron salt as the metal precursor, benzenetricarboxylic as the organic compound and the inorganic acid comprising nitric acid and hydrofluoric acid in a molar ratio of 0.1~1:1~0.1 as the acid, is prepared by stirring or by irradiating with supersonic waves to form crystal nuclei and is heated at the temperature of 100° C. to 250° C.

11. The method as set forth in claim 1, wherein the porous organic-inorganic hybrid materials are prepared in a form of thin film, pellet or membrane.

* * * * *